US00PP29487P2

(12) United States Plant Patent
Tuinier

(10) Patent No.: US PP29,487 P2
(45) Date of Patent: Jul. 10, 2018

(54) ***SENECIO* PLANT NAMED 'SI SEN 1005'**

(50) Latin Name: ***Senecio cephalophorus* x *Senecio fulgens***
Varietal Denomination: SI SEN 1005

(71) Applicant: Wander Durk Tuinier, Krimpen aan den IJssel (NL)

(72) Inventor: Wander Durk Tuinier, Krimpen aan den IJssel (NL)

(73) Assignee: Dümmen Group B.V., De Lier (NL)

( * ) Notice: Subject to any disclaimer, the term of this patent is extended or adjusted under 35 U.S.C. 154(b) by 0 days.

(21) Appl. No.: 15/530,823

(22) Filed: Mar. 3, 2017

(51) Int. Cl.
*A01H 5/12* (2018.01)

(52) U.S. Cl.
USPC ..... Plt./373

(58) Field of Classification Search
USPC ..... Plt./373
See application file for complete search history.

*Primary Examiner* — Annette H Para
(74) *Attorney, Agent, or Firm* — C. A. Whealy

(57) ABSTRACT

A new and distinct cultivar of *Senecio* plant named 'SI SEN 1005', characterized by its uniform, upright and bushy plant habit; flat obovate leaves; medium green-colored leaves covered with a greyed green-colored cuticle with distinct pale green-colored venation; and excellent interiorscape performance.

2 Drawing Sheets

Botanical designation: *Senecio cephalophorus* x *Senecio fulgens.*

Cultivar denomination: 'SI SEN 1005'.

BACKGROUND OF THE INVENTION

The present invention relates to a new and distinct cultivar of *Senecio* plant, botanically known as *Senecio cephalophorus* x *Senecio fulgens*, and hereinafter referred to by the name 'SI SEN 1005'.

The new *Senecio* plant is a product of a planned breeding program conducted by the Inventor in Krimpen aan den IJssel, The Netherlands. The objective of the breeding program was to develop new and distinct *Senecio* plants with good interiorscape performance.

The new *Senecio* plant originated from a cross-pollination made by the Inventor in 2012 of *Senecio cephalophorus* 'Mountain Fire', not patented, as the female, or seed, parent with *Senecio fulgens* 'Mandarin', not patented, as the male, or pollen, parent. The new *Senecio* plant was discovered and selected as a single plant within the progeny of the stated cross-pollination in a controlled environment in Krimpen aan den IJssel, The Netherlands.

Asexual reproduction of the new *Senecio* plant by tip cuttings in a controlled environment in Krimpen aan den IJssel, The Netherlands since March, 2014 has shown that the unique features of this new *Senecio* plant are stable and reproduced true to type in successive generations.

SUMMARY OF THE INVENTION

Plants of the new *Senecio* have not been observed under all possible combinations of environmental conditions and cultural practices. The phenotype may vary somewhat with variations in environmental conditions such as temperature and light intensity, without, however, any variance in genotype.

The following traits have been repeatedly observed and are determined to be the unique characteristics of 'SI SEN 1005'. These characteristics in combination distinguish 'SI SEN 1005' as a new and distinct *Senecio* plant:

1. Uniform, upright and bushy plant habit.
2. Flat obovate leaves.
3. Medium green-colored leaves covered with a greyed green-colored cuticle with distinct pale green-colored venation.
4. Excellent interiorscape performance.

Plants of the new *Senecio* differ primarily from plants of the female parent, 'Mountain Fire', in leaf color as plants of 'Mountain Fire' have grey green-colored leaves without distinct venation.

Plants of the new *Senecio* differ primarily from plants of the male parent, 'Mandarin', in the following characteristics:

1. Plants of the new *Senecio* are more freely branching and bushier than plants of 'Mandarin'.
2. Leaves of plants of the new *Senecio* are not as round as leaves of plants of 'Mandarin'.
3. Plants of the new *Senecio* and 'Mandarin' differ in leaf color as leaves of plants of 'Mandarin' are pale green in color with grey-colored venation.

Plants of the new *Senecio* can be compared to plants of *Senecio cephalophorus* 'Tanzanite', not patented. In side-by-side comparisons, plants of the new *Senecio* differ primarily from plants of 'Tanzanite' in leaf color as plants of 'Tanzanite' have grey green-colored leaves without distinct venation.

Plants of the new *Senecio* can also be compared to plants of *Senecio cephalophorus* 'Fuji', not patented. In side-by-side comparisons, plants of the new *Senecio* differ primarily from plants of 'Fuji' in the following characteristics:

1. Plants of the new *Senecio* are more freely branching and bushier than plants of 'Fuji'.
2. Plants of the new *Senecio* and 'Fuji' differ in leaf color as leaves of plants of 'Fuji' are pale green in color without distinct venation.

BRIEF DESCRIPTION OF THE PHOTOGRAPHS

The accompanying colored photographs illustrate the overall appearance of the new *Senecio* plant showing the colors as true as it is reasonably possible to obtain in colored reproductions of this type. Colors in the photographs may differ slightly from the color values cited in the detailed botanical description which accurately describe the colors of the new *Senecio* plant.

The photograph on the first sheet comprises a top perspective view of a typical plant of 'SI SEN 1005' grown in a container.

The photograph on the second sheet is a close-up view of a typical plant of 'SI SEN 1005' grown in a container.

DETAILED BOTANICAL DESCRIPTION

The aforementioned photographs and following observations, measurements and values describe plants grown during the winter in 10.5-cm containers in a glass-covered greenhouse in Krimpen aan den IJssel, The Netherlands and under cultural practices typical of commercial *Echeveria* production. During the production of the plants, day temperatures ranged from 18° to 25° C. and night temperatures ranged from 15° to 18° C. Plants were 30 weeks old when the photographs and description were taken. In the following description, color references are made to The Royal Horticultural Society Colour Chart, 2015 Edition, except where general terms of ordinary dictionary significance are used.

Botanical classification: *Senecio cephalophorus*×*Senecio fulgens* 'SI SEN 1005'.

Parentage:

*Female, or seed, parent.*—*Senecio cephalophorus* 'Mountain Fire', not patented.

*Male, or pollen, parent.*—*Senecio fulgens* 'Mandarin', not patented.

Propagation:

*Type*.—By tip cuttings.

*Time to initiate roots, summer*.—About seven days at temperatures about 20° C.

*Time to initiate roots, winter*.—About ten days at temperatures about 20° C.

*Time to produce a rooted young plant, summer and winter*.—About 30 days at temperatures about 20° C.

*Root description*.—Fine; typically white in color, actual color of the roots is dependent on substrate composition, water quality, fertilizer type and formulation.

*Rooting habit*.—Freely branching; dense.

Plant description:

*Plant form and growth habit*.—Herbaceous perennial plant; uniform, upright and bushy plant habit; short internodes with flat obovate leaves; low to moderate vigor and growth rate.

*Plant height*.—About 12.1 cm.

*Plant diameter*.—About 20.5 cm.

*Lateral branches*.—Branching habit: Basally branching habit; about five primary branches develop, each with about five secondary branches; pinching enhances lateral branch development. Length: About 9.4 cm. Diameter: About 6 mm. Internode length: About 0.3 mm. Strength: Moderately strong. Aspect: About 35° from vertical. Texture: Smooth, glabrous; waxy; succulent. Luster: Slightly glossy. Color: Developing: Close to 144B to 144C; waxy cuticle, close to 142D. Developed: Close to 144B to 144C; waxy cuticle, close to 190D.

Leaf description:

*Arrangement*.—Alternate, simple.

*Length*.—About 3.3 cm.

*Width*.—About 2.2 cm.

*Thickness*.—About 1.25 mm.

*Shape*.—Obovate.

*Apex*.—Abruptly acute.

*Base*.—Attenuate.

*Margin*.—Mostly entire; occasionally slightly serrate with one or two very small teeth towards the apex.

*Texture, upper and lower surfaces*.—Smooth, glabrous; waxy.

*Luster, upper and lower surfaces*.—Matte.

*Venation pattern*.—Pinnate.

*Color*.—Developing leaves, upper surface: Close to 137A to 137B; waxy cuticle, close to 190D; venation, close to 147D. Developing leaves, lower surface: Close to 137B; waxy cuticle, close to 190B. Fully expanded leaves, upper surface: Close to NN137C; waxy cuticle, close to 190B; venation, close to 138C. Fully expanded leaves, lower surface: Close to NN137C; waxy cuticle, close to 190B; venation, close to 138B to 138C.

*Petioles*.—Length: About 1.7 cm. Diameter: About 2 mm to 4 mm. Strength: Moderate. Aspect: Mostly horizontal. Texture: Smooth, glabrous. Luster: Matte. Color, upper and lower surfaces: Close to 144B; waxy cuticle, close to 142D.

Flower description: To date, flower initiation and development have not been observed on plants of the new *Senecio*.

Disease & pest resistance: Plants of the new *Senecio* have not been observed to be resistant to pathogens and pests common to *Senecio* plants.

Temperature tolerance: Plants of the new *Senecio* have been observed to tolerate temperatures ranging from about 10° C. to about 40° C. and to be suitable for USDA Hardiness Zones 10 to 12.

It is claimed:

1. A new and distinct *Senecio* plant named 'SI SEN 1005' as illustrated and described.

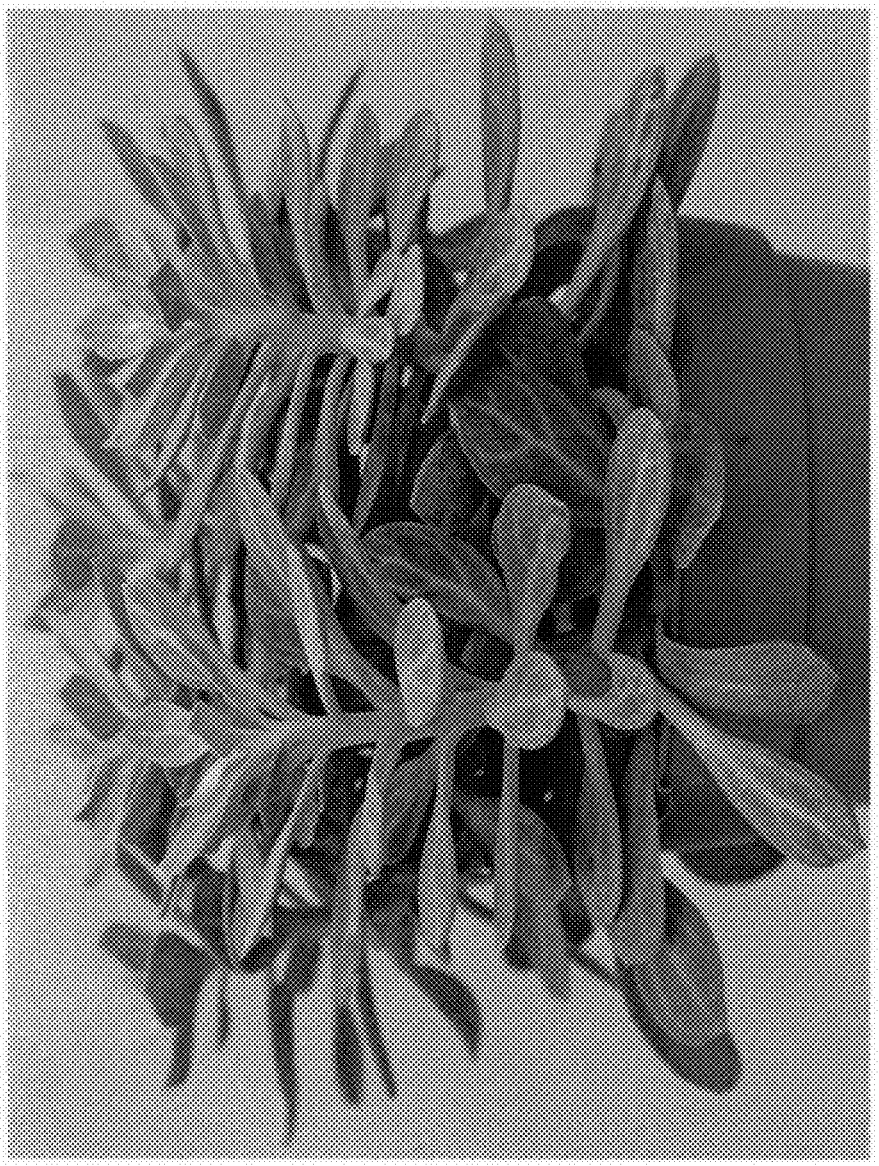

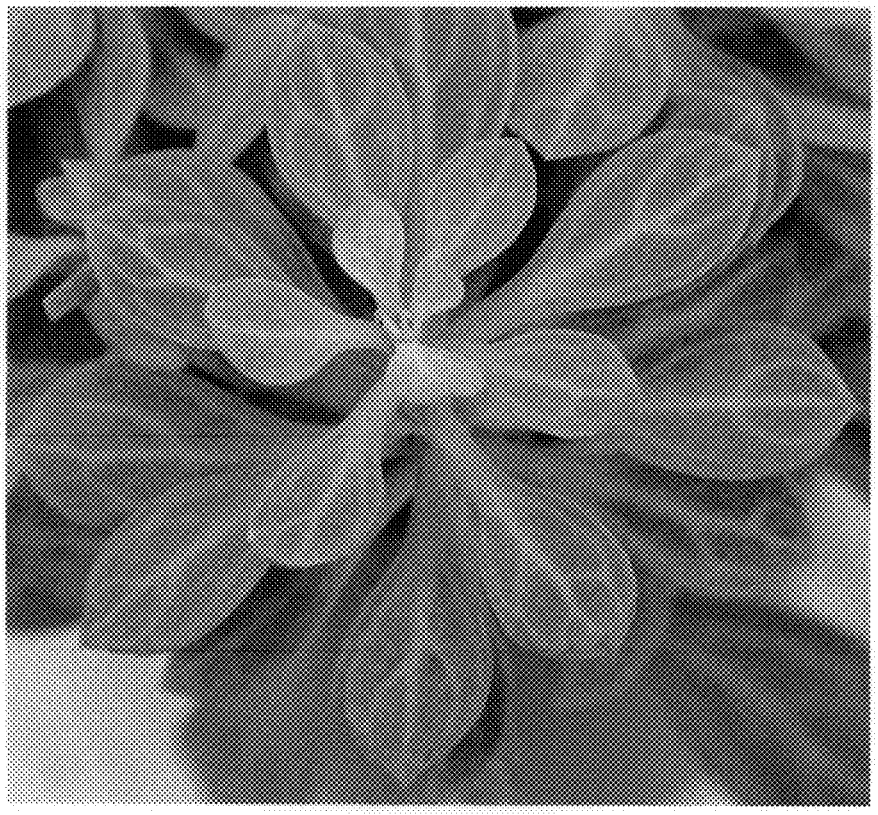

* * * * *